(12) United States Patent
Gilton (10) Patent No.: US 7,777,287 B2
(45) Date of Patent: Aug. 17, 2010

(54) SYSTEM AND APPARATUS PROVIDING ANALYTICAL DEVICE BASED ON SOLID STATE IMAGE SENSOR

(75) Inventor: Terry Gilton, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 577 days.

(21) Appl. No.: 11/484,706

(22) Filed: Jul. 12, 2006

(65) Prior Publication Data
US 2008/0012083 A1    Jan. 17, 2008

(51) Int. Cl.
*H01L 31/232*    (2006.01)
(52) U.S. Cl. ............... 257/432; 257/443; 257/431; 257/433; 257/434; 257/435; 257/436; 257/437; 257/438; 257/439; 257/440; 257/441; 257/442; 257/E31.001
(58) Field of Classification Search ......... 257/431–433, 257/E31.001
See application file for complete search history.

(56) References Cited

U.S. PATENT DOCUMENTS

| 6,221,687 B1 | 4/2001 | Abramovich |
| 6,905,834 B1 | 6/2005 | Simpson et al. |
| 2005/0110989 A1 | 5/2005 | Schermer et al. |
| 2006/0029522 A1 | 2/2006 | Theil |

FOREIGN PATENT DOCUMENTS

| DE | 102 21 885 A1 | 12/2003 |
| DE | 10 2004 015272 A1 | 11/2005 |
| WO | WO 2005/019822 A | 3/2005 |

OTHER PUBLICATIONS

Yasaman Ardeshirpour, et al., Abstract, Two-dimensional CMOS-based image sensor system for fluorescent detection, Can. J. Elect. Comput. Eng., vol. 29, No. 4, Oct. 2004.
T. J. Thornton, et al., Hybrid Biomolecular-CMOS Integrated Circuits, http://photoscience.la.asu.edu/bionano/research6.htm.
Dr. Blair, Research, Optical Biosensor Arrays, http://www.ece.utah.edu~blair/R/research.html.
Kenneth Shepard, CMOS biochips, http://www.ceisRochester.edu/ceis/mdc/projects.

*Primary Examiner*—Cuong Q Nguyen
*Assistant Examiner*—Trang Q Tran
(74) *Attorney, Agent, or Firm*—Dickstein Shapiro LLP (57) ABSTRACT

An analytical system-on-a-chip can be used as an analytical imaging device, for example, for detecting the presence of a chemical compound. A layer of analytical material is formed on a transparent layer overlying a solid state image sensor. The analytical material can react in known ways with at least one reactant to block light or to allow light to pass through to the array. The underlying sensor array, in turn, can process the presence, absence or amount of light into a digitized signal output. The system-on-a-chip may also include software that can detect and analyze the output signals of the device.

20 Claims, 8 Drawing Sheets

SYSTEM AND APPARATUS PROVIDING ANALYTICAL DEVICE BASED ON SOLID STATE IMAGE SENSOR

FIELD OF THE INVENTION

The invention relates generally to analytical devices and more particularly to analytical devices that use image sensors for detection.

BACKGROUND

Solid state imagers are increasingly popular due to small size, low cost, and improved image quality. One such solid state imager is a CMOS imager. CMOS sensor technology enables a higher level of integration of an image array with associated processing circuits, which can be beneficial to many digital applications such as, for example, in cameras, scanners, machine vision systems, vehicle navigation systems, video telephones, computer input devices, surveillance systems, auto focus systems, star trackers, motion detection systems, image stabilization systems and other imaging applications.

A CMOS imager circuit includes a focal plane array of pixel cells, each one of the cells including a photosensor, for example, a photogate, photoconductor or a photodiode overlying a substrate for accumulating photo-generated charge in the underlying portion of the substrate. Each pixel cell has a readout circuit that includes at least an output field effect transistor formed in the substrate and a charge storage region formed on the substrate connected to the gate of an output transistor. The charge storage region may be constructed as a floating diffusion region. Each pixel may include at least one electronic device such as a transistor for transferring charge from the photosensor to the storage region and one device, also typically a transistor, for resetting the storage region to a predetermined charge level prior to charge transference.

In a CMOS imager, the active elements of a pixel cell, as just described, perform the necessary functions of: (1) photon to charge conversion; (2) accumulation of image charge; (3) resetting the storage region to a known state; (4) selection of a pixel for readout; and (5) output and amplification of a signal representing pixel charge. The charge at the storage region is typically converted to a pixel output voltage by the capacitance of the storage region and a source follower output transistor.

CMOS imagers of the type discussed above are generally known as discussed, for example, in U.S. Pat. No. 6,140,630, U.S. Pat. No. 6,376,868, U.S. Pat. No. 6,310,366, U.S. Pat. No. 6,326,652, U.S. Pat. No. 6,204524 and U.S. Pat. No. 6,333,205, assigned to Micron Technology, Inc., which are hereby incorporated by reference in their entirety.

Due to the sensing capabilities of CMOS and other solid state image sensors, such sensors can be used as analytical devices. Based on advantages such as low-cost production and lower power consumption, CMOS image sensors may be particularly well suited for this purpose. The analytical devices can be useful for a range of applications, including clinical screening, detection of environmental contaminants, and gene hybridization.

There are known examples of using luminescent bioreporters that include CMOS integrated circuits. For example, in U.S. Pat. No. 6,905,834, bioluminescent bacteria are placed on specially-designed integrated circuits that include CMOS pixel sensors, each with a photodiode. The bacteria are designed to produce a luminescence in response to metabolizing a targeted substance. The CMOS pixel sensors are capable of sensing the incoming luminescence and converting it to a digitized, output signal. These bioreporters can be used for detecting a variety of substances.

While the devices discussed in U.S. Pat. No. 6,905,834 have potential for application in a number of contexts, the use of bacterial substances may make the disclosed bioreceptors less desirable in other contexts. In addition, depending on the source of the bacteria, the disclosed bioreceptors could be costly to produce and may have a limited shelf-life. In addition, these bioreceptors are designed using materials that fluoresce (i.e., put out light) when exposed to certain substances. Thus, these devices are limited in the materials that can be used for detection and in the substances that they can be used to detect.

Thus, it is desirable to have an analytical device, using solid state image sensors, for example, CMOS sensors, to detect and report reactions, such as exposure to a compound under test, that can be useful with a vast number of compounds and that can be easily and cost-effectively produced. Simple methods of fabricating the analytical devices are also needed.

SUMMARY

The invention provides an analytical system-on-a-chip that can be used as an analytical device, for example, to detect the presence of a chemical compound. In one exemplary embodiment, the invention provides a layer of analytical material that is formed on a transparent layer overlying an image sensor array. The analytical material can react with a series of species of interest in various ways to block light or to allow light to pass through. The underlying sensor array provides signals which are processed as digital signals on the chip to provide analytical information as an output.

In accordance with another aspect of the invention, a method of fabricating the analytical system-on-a-chip is disclosed, including the acts fabricating sensing and analytical circuitry which can be used to detect and/or analyze at least one reactant material applied to the system.

In a preferred embodiment, the invention may be implemented using a CMOS image sensor which can be built both cost-and size-efficiently. In addition, the formed device can be disposable or reusable depending on the materials used in fabrication.

BRIEF DESCRIPTION OF THE DRAWINGS

The foregoing and other advantages and features of the invention will become more apparent from the detailed description of exemplary embodiments provided below with reference to the accompanying drawings in which.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized, and that structural, logical and electrical changes may be made without departing from the spirit and scope of the present invention.

The terms "wafer" and "substrate" are to be understood as a semiconductor-based material including silicon, silicon-on-insulator (SOI) or silicon-on-sapphire (SOS) technology, doped and undoped semiconductors, epitaxial layers of silicon supported by a base semiconductor foundation, and other semiconductor structures. Furthermore, when reference is made to a "wafer" or "substrate" in the following description, previous process steps may have been utilized to form regions or junctions in or over the base semiconductor structure or foundation. In addition, the semiconductor need not be silicon-based, but could be based on silicon-germanium, silicon-on-insulator, silicon-on-saphire, germanium, or gallium arsenide, among others. The term "pixel" refers to a picture element unit cell containing a photosensor and one or more transistors for converting electromagnetic radiation to an electrical signal.

Figure 1:
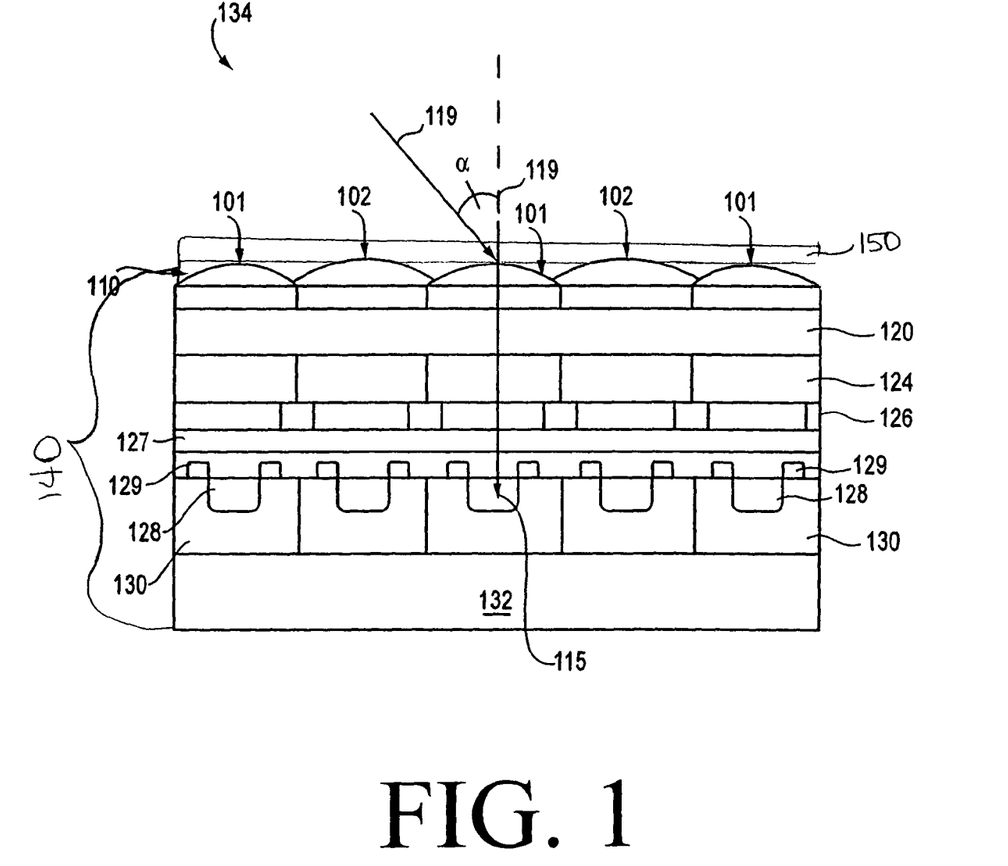
FIG. 1 illustrates a cross-sectional view of a portion of an analytical, imaging device in accordance with a first exemplary embodiment of the invention.
Figure 2:
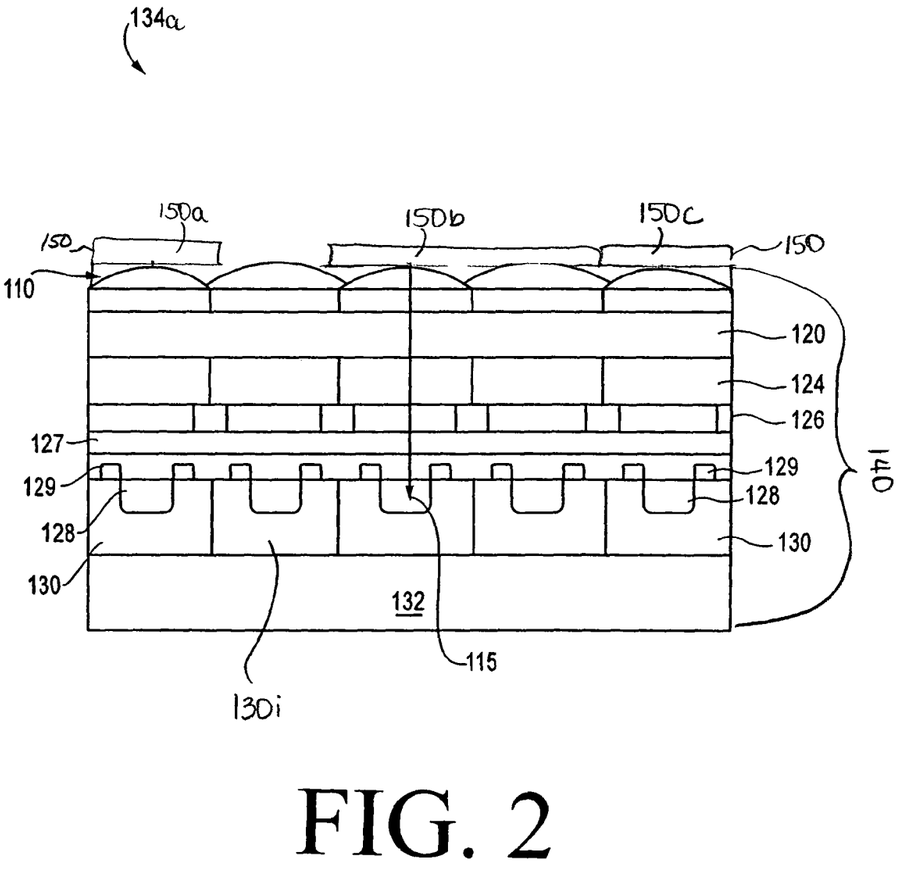
FIG. 2 illustrates a cross-sectional view of a portion of an analytical, imaging device in accordance with a second exemplary embodiment of the invention.
Figure 3:
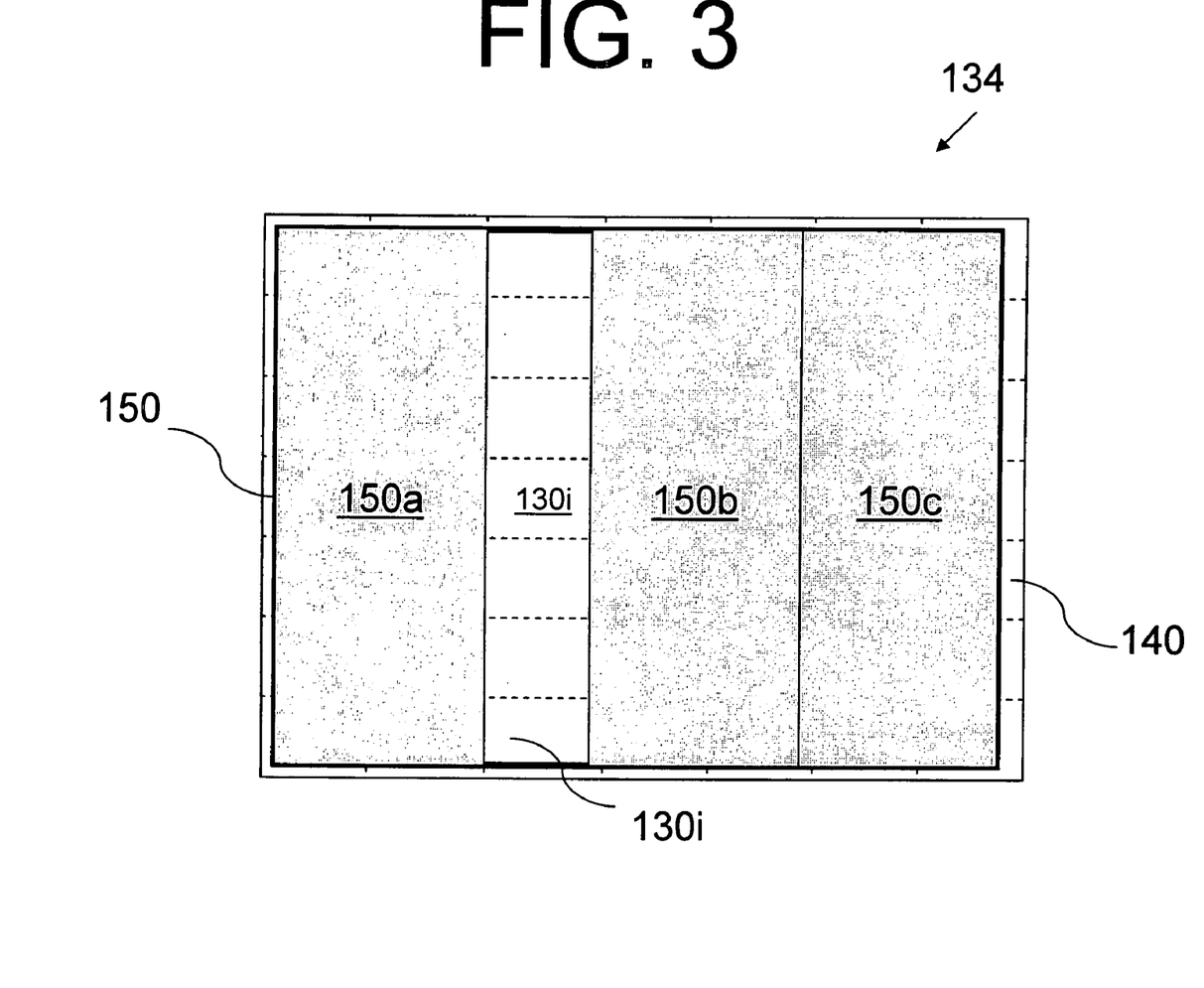
FIG. 3 illustrates a top down view of the exemplary analytical imaging device shown in FIG. 2.

Now turning to the figures, where like numbers represent like elements, FIG. 1 shows a side-view of portions of an exemplary analytical imaging device 134 which can be used for detecting, identifying and/or analyzing substances, such as chemical compounds that may or may not be known. The illustrated imaging device 134 has a material layer 150 that is formed over and adhered to a CMOS image sensor package 140. FIGS. 2 and 3 show a side-and top-down view, respectively, for a second exemplary analytical imaging device 134a which also has a material layer 150 (described below) useful for detecting, identifying and analyzing substances.

It should be understood that the term "material layer" 150 as used herein may include one type of material formed to either partially or fully cover the package 140, as shown in FIG. 1, or it may include multiple materials 150a, 150b, 150c formed, for example, in one substantially planar level over the image sensor package 140 as shown in FIGS. 2-3. Alternatively, the multiple analytical materials 150a, 150b, 150c may be formed in stacked, or non-planar, levels over the package 140. The material layer 150 may include different materials 150a, 150b, 150c scattered in a pre-determined pattern over the image sensor package 140. Thus, although the term is used in the singular form herein, it should be understood that "material layer 150" may include multiple materials. The material layer 150 is useful in exemplary identification/detection processes performed using the analytical imaging device 134, as described in more detail below.

In a preferred embodiment, the material layer 150 is transparent or semi-transparent such that incoming light rays 119 pass through the material layer 150 where they are focused onto underlying photosensors 128 by a microlens array 110. For example, the material layer 150 may be a form of glass or a transparent amorphous polymer. In another embodiment, the material layer 150 is opaque, but may become transparent or may dissolve completely when exposed to a particular reactant. For example, the material layer may be formed of an opaque or semi-transparent latex rubber layer which, when reacted with a non-polar organic solvent, such as toluene, may dissolve. The invention, however, is in no way limited to the types of materials used for the analytical imaging devices 134, 134a.

In one embodiment of the invention, materials are selected such that manufacturing costs are minimized so that the analytical imaging device 134 can be disposable. In another embodiment the materials may be selected so that the analytical imaging device 134 can be reclaimed after use for repeated usage. For example, the analytical imaging device 134 can include a material layer 150 and package 140 which are removable from the underlying solid state image sensor, such that the image sensor can be reused with a replaced package 140. In fact, the image sensor could be reused with a replaced package 140 including a material layer 150 for continuing use as an analytical imaging device 134. In addition, the material layer 150 may be removable so that the package 140 is reusable after removing the material layer 150. In accordance with other aspects of the invention, materials may be selected so that the size of the analytical imaging device 134 is minimized. Other considerations when selecting materials will be discussed below.

As shown in the illustrated exemplary embodiments of FIG. 1-2, the analytical imaging devices 134, 134a include a pixel sensor array that is composed of numerous CMOS pixel sensors 130 formed in association with a semiconductor substrate 132 in a repeating pattern of rows and columns (as shown in dashed outline form in FIG. 3). A microlens array 110, with a plurality of microlenses 101, 102 formed on a receiving surface 120 of the package 140 may be provided between the semiconductor substrate 132 and the material layer 150. Beneath the microlens array 110 may be a color filter array 124 (if needed for color applications), a light shield layer 126, at least one inter-level dielectric (ILD) layer 127, which also may encompass metal wiring interconnects (not shown), and pixel cells 130 fabricated on the substrate 132. Additional layers, such as additional BPSG and ILD layers may also be a part of the an analytical imaging device 134 as known in the art. Each pixel 130 includes transistors 129 and a photosensor 128, which may be any type of photosensor, including but not limited to a photogate or photodiode. The light shield 126 and metallization layers may be formed to block light from reaching the other light sensitive parts of the pixels 130, so that incident light is directed mainly to the photosensors 128.

The material layer 150 can be formed in many different ways in accordance with the invention. For example, the material layer 150 may be formed of one known chemical compound, such as a known polymer. In another embodiment, the material layer 150 is made of more than one polymer, each polymer being formed over a set of pixels 130 in the pixel array. For example, as illustrated in FIG. 2, the material layer 150 may include several materials 150a, 150b, 150c, which can be different polymers, each formed over one or more underlying pixels 130. The polymers may all be pre-known, when the analytical imaging device 134 or 134a is to be used for determining the identity of one or more unknown reactants. Alternatively, the material layer 150 can be formed of an unknown substance, and used in connection with known reactants to determine the identity of the material layer 150.

As an example, the material layer 150 can be made of a thin layer of leaded crystal. A section of the material layer 150 may be leaded crystal that has been treated with a substance such as lead sulfide, which darkens the crystal and makes it less transparent. If the material layer 150 is exposed to the appropriate reactant, in this case a nitric acid solution, the lead sulfide is removed from the crystal, making it clear again. Thus, this exemplary method could be used to identify or detect the presence of nitric acid.

In addition, the invention is in no way limited to a particular means for adhering the material layer 150 to the image sensor device package 140. For example, the material layer itself 150 can be composed of an adhesive substance and therefore would adhere to the package 140 by simply applying pressure to the two substances. Alternatively, the material layer 150 could be formed on a transparent substrate layer (not shown) and this transparent substrate layer could then be adhered to the package 140 using any known transparent adhesive. As another alternative, the material layer 150 may be formed directly on the outer surface of the package 140.

The material layer 150 can be formed over a large number of underlying pixel sensors 130 in the pixel array. As shown in FIGS. 2 and 3 illustrating one exemplary embodiment, however, at least one pixel 130i can be left uncovered by the material layer 150. These are referred to as "white" pixels. In addition, the analytic imaging device 134 or 134a may be formed such that one or more pixels are covered by a blocking object, such as underlying circuitry or a non-transparent light shielding layer 126, so that the pixels do not receive incoming light. These are referred to as "black" pixels. These black and white pixels 130i will be used as references during the analytical process as described in more detail herein. Specifically, these reference pixels are used in calibration of the analytical imaging device 134 or 134a.

Figure 4:
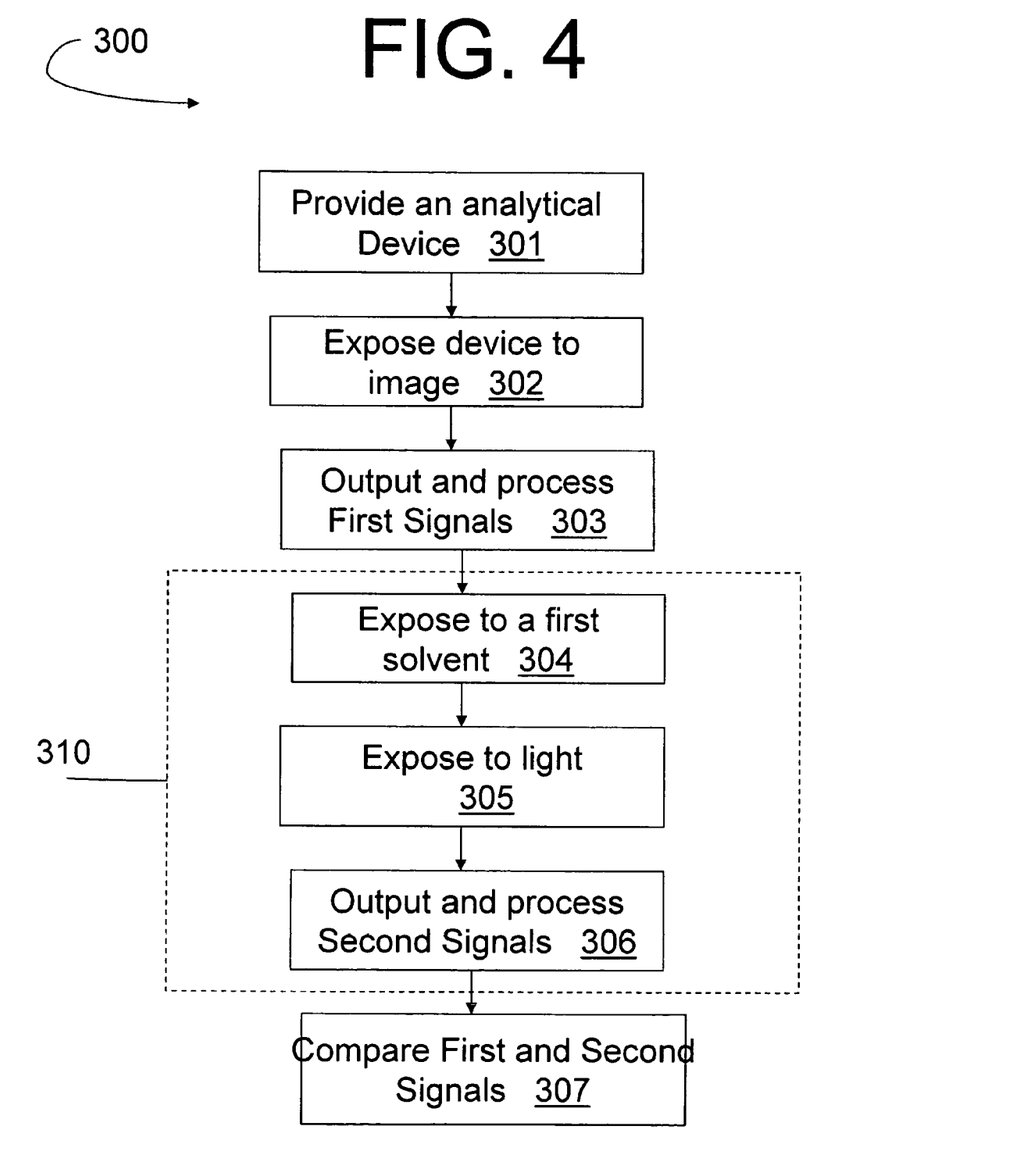
FIG. 4 illustrates an exemplary method of utilizing an analytical imaging device in accordance with the invention.

FIG. 4 is a flowchart illustrating an exemplary method 300 of using the analytical device 134 in accordance with the invention. The first step 301 in the exemplary method 300, is to provide an analytical imaging device 134, which may be according to any of the embodiments as described above. Next, at step 302, the analytical imaging device 134 is exposed to a light source. At step 303, the photoconversion devices 128 for pixels 130 in combination with the circuitry 129 create pixel signals for a plurality of pixels 130 in the analytical imaging device 134 based on the applied image. These signals are output from the pixels 130. In one exemplary embodiment, the pixel signals are output and processed by circuitry on a chip with the analytical imaging device 134. It should be understood that the pixel signals could also be output to and processed by external processing memories and circuitry. Additionally, if the signals are externally processed, a system including the imaging device 134 may include circuitry for wirelessly transmitting information, including the pixel signals.

Returning to FIG. 4, at this point, the first signals output during step 303 represent a non-altered state for the imaging device 134. Preferably, these first signals are stored in memory. Next, at step 304, the material layer 150 of the analytical imaging device 134 is exposed to a first reactant. For example, the analytical imaging device 134 may be dipped into a liquid solvent. Alternatively, a reactant could be applied as a liquid or vapor to the whole or some portion of the material layer 150. The exemplary method 300 is not limited to a means for application of the reactant to the material layer 150, and the method for application may depend on the particular materials involved.

The reactant may or may not react with the material layer 150. The reactant may completely dissolve the material layer 150. The reactant may react in a way that changes the characteristics, including the optical characteristics, of the material layer 150. For example, the reactant may cause the transparent material layer 150 substance to be less transparent or opaque, therefore allowing less light 119 to pass through to underlying pixels 130. There are innumerable possibilities for the reactions between the material layer 150 and the reactant. For example, the reactant may react with only one or some of the substances 150a, 150b, 150c that make up the material layer 150. On the other hand, the applied reactant may be completely unreactive with the material layer 150 substance (s).

It should be further explained that as mentioned above, the device 134 is used to identify unknown substances. Either the identity of the material layer 150 substance(s) or the identity of the reactant will thus likely be unknown. If the identity of the material layer 150 is known, the identity of the reactant will likely be unknown. Correspondingly, if the identity of the applied reactant is known, the identity of the substance(s) of the material layer 150 can be determined. Preferably, for whichever substance(s) are known, the characteristics and reactivities of this substance(s) are also known before operation. As an alternative, the analytical imaging device 134 may be used for analyzing properties of known substances. In this instance, the identities of both the material layer 150 and the applied reactant may be known.

Returning to the exemplary method 300, at step 305, a light source is applied to the analytical imaging device 134 including the material layer 150 having been exposed to the reactant. If reference pixels are utilized as discussed above, there is no need for the light source at this step to be the same as the light source at step 302. On the other hand, one continuous light source or image can be used for both steps 302 and 305. Similar to step 303, at step 306, second pixel output signals are generated and output from pixels 130 representing the second application of a light image. In addition, it should also be understood that steps 304 and 305 can occur simultaneously; that is, the analytical imaging device can be exposed to light as it is being exposed to the analyte.

Finally, at step 307, the first pixel output signals from step 303 and the second pixel output signals from step 306 are compared and analyzed. In a preferred method, the analytical device includes both black and white pixels that are used as reference pixels. Thus, the black pixels received no light during the light exposure steps 302, 305 and their first and second output signals therefore represent a no-light condition before and after application of the reactant, respectively. At the other extreme, the signals from the white pixels 130i having no coverage by a material layer 150 should, even after application of the reactant, represent a full exposure or "bright" signal. In between the output of the white and black pixels, should be a range of signals from pixels 130 covered by material layer 150 but receiving some amount of light depending on: (i) the optical characteristics of the material layer 150 before application of the reactant and (ii) the optical characteristics after application and possible reaction with the reactant.

The analysis process at step 307 therefore may comprise a comparison of the first pixel output signals between normal pixels and the reference pixels before application of the reactant as well as a comparison of the first and second sets of pixel output signals to one another. Put another way, a first step of the analysis may comprise determining the optical characteristics of the material layer 150 before application of the reactant by comparing the first output of a white pixels 130i to the first output of other pixels 130 covered by the material layer 150 but otherwise receiving light. Next, a similar comparison can be done with the second signals to determine the optimal characteristics of the material layer 150 after application of the reactant. Thus, by comparing the change (if any) to the optical characteristics of the material layer 150 after application of a reactant, the identity of the unknown substance, whether it be the material layer 150 or the reactant, can be determined, assuming that the possible reactivities of the known substance are known.

Depending on the use of the analytical imaging device 134, other comparisons at step 307 may be made. For example, both the substance of the material layer 150 and the reactant could be known; in which case, this method 300 is carried out to determine the reactivity or change in characteristics of the substances when introduced. As another alternative, the analytical imaging device 134 may be used to determine the presence of a particular substance in a location, which in this case would be the reactant. Thus, a material layer 150 would be formed of a material that has a known reaction with the particular substance under investigation. By analyzing the output signals from pixels 130 in the device 134 when in the location, it can be determined whether or not the substance under investigation is present.

Figure 4A:
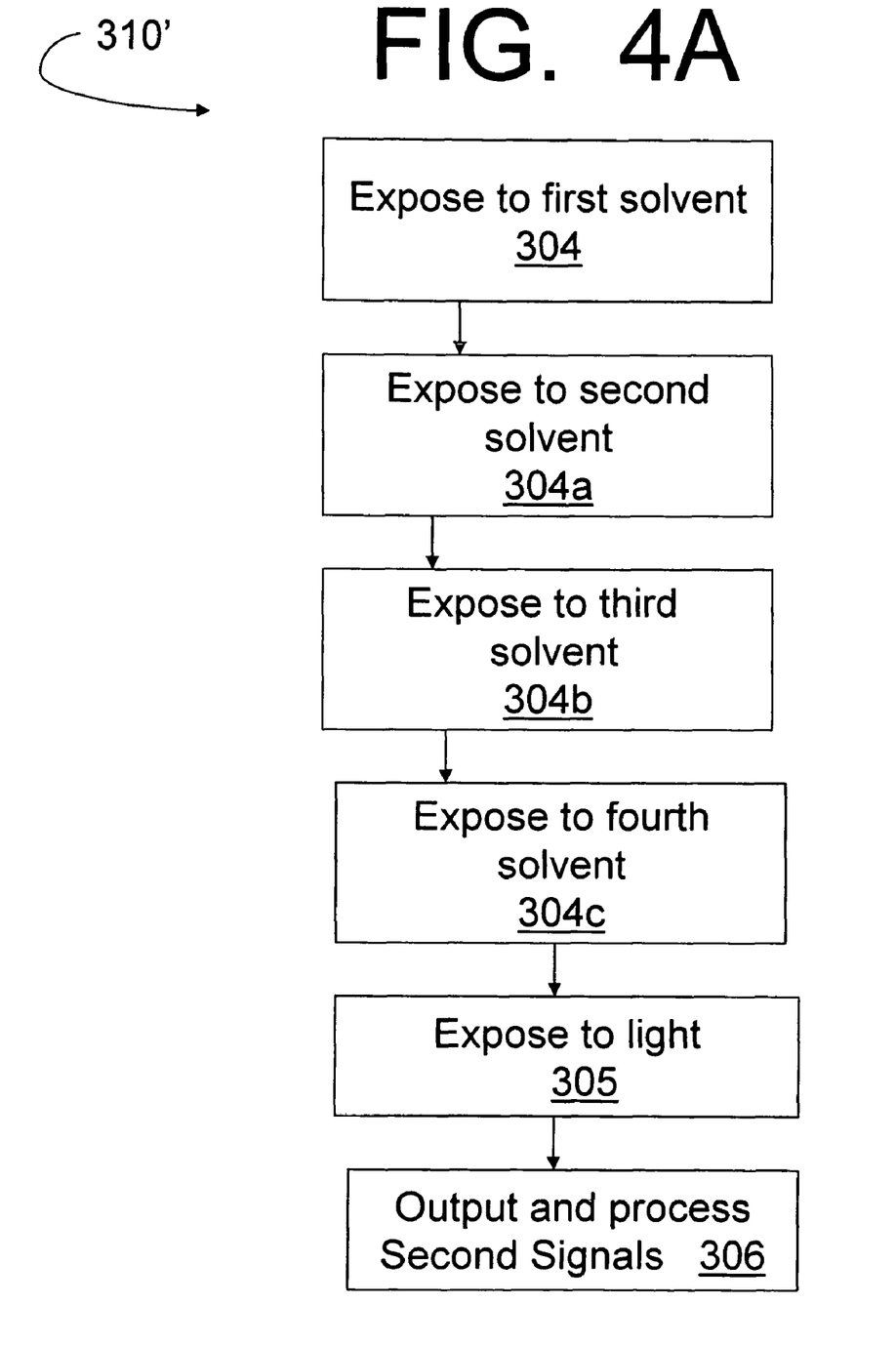
FIG. 4A illustrates a repeatable portion of the exemplary method of FIG. 4 in accordance with a first exemplary embodiment.

It should also be noted that section 310 of the method 300 can be repeated for application of more than one reactant. The repeated portion 310 of the method 300 can be performed in at least two ways. As shown in FIG. 4A, repeated portion 310' may include steps 304a, 304b, 304c in which second, third, and fourth reactants, respectively, are applied to the material layer 150. This can also be done in numerous ways, for example, by applying one reactant respectively to each of numerous substances 150a, 150b, 150c that make up the material layer 150. It should be understood that this sequence of steps can also be done with any number of reactants applied using any application technique(s), which do not necessarily need to be the same for each reactant. After this, the repeated portion 310' proceeds with steps 305 and 306 as described above with reference to FIG. 4. The identity of numerous reactants could be determined thereafter by comparing the pixel output signals.

Figure 4B:
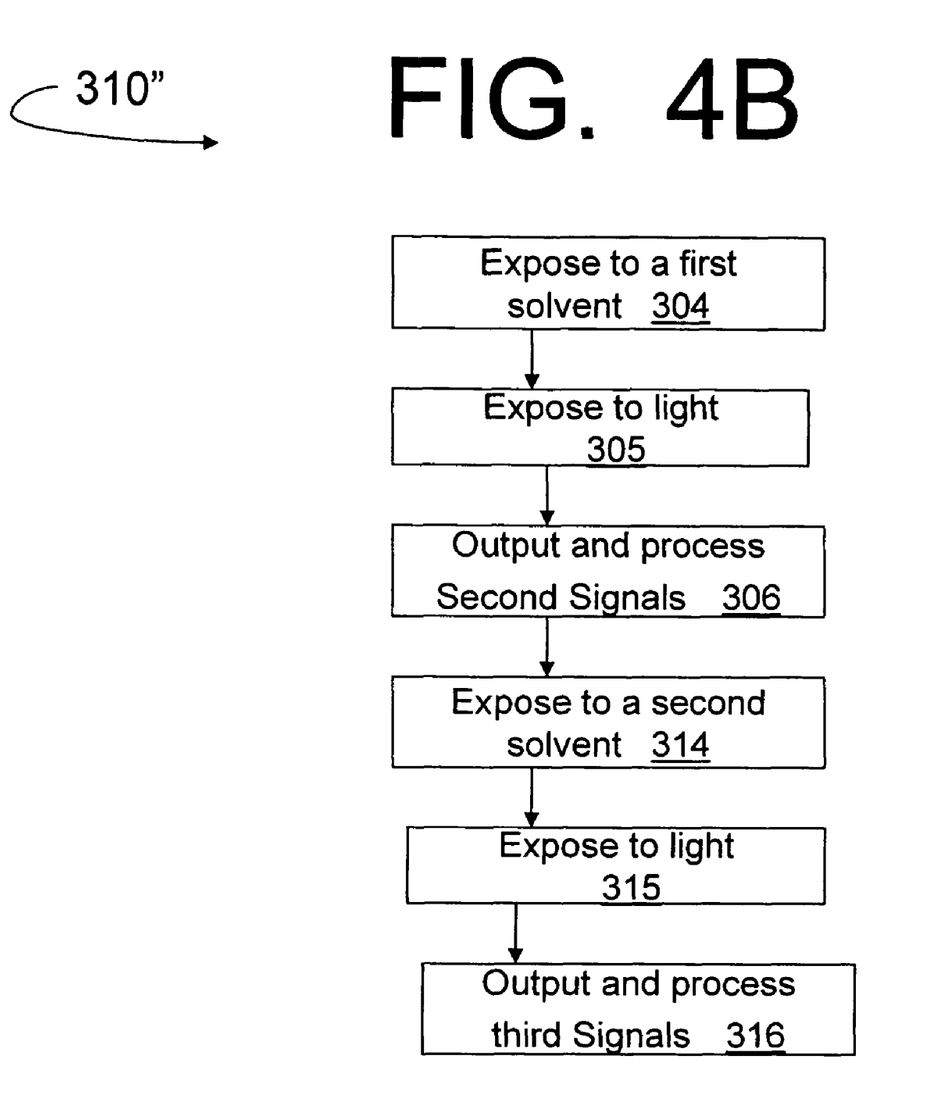
FIG. 4B illustrates a repeatable portion of the exemplary method of FIG. 4 in accordance with a second exemplary embodiment.

In another exemplary method, a portion of which is illustrated in FIG. 4B, the repeated portion 310' includes additional steps after steps 304-306 described above, the first of which is exposure to a second reactant at step 314. As above, this may include exposure of the reactant to the entire or any part of the material layer 150. Next, the material layer 150 which has now been exposed to two reactants, is exposed to a light source or image at step 315. A third set of pixel signals is then output from the pixels for processing at step 316. Thereafter, processing and analysis of first, second and third pixel output signals can be used for identifying the unknown substance(s).

The processing described for the exemplary method 300 may be done by processing software. This processing software may be in an image processor 580 (FIG. 5) that is located on a chip with the analytical imaging device 134. The software may include functionality for determining the identity of one or more of the unknown substances in the analytical imaging device 134. For example, a look-up table including predicted results can be stored in a processing memory for performing an automated look-up procedure. This look-up table could include known results for reactions between materials that make up the material layer 150 and the applied reactants. Thus, when the output pixel signals are used to determine a change in characteristics of the material layer 150, this change can be compared with predicted changes for the materials involved to determine the unknown reactant.

In another embodiment, the look-up process is not automated but is done by operators utilizing the analytical device 134. In this way, an operator of the analytical device 134 receives output data representing the first and second pixel signals from steps 303, 306 (FIG. 4). Applying these results, the operator can then determine the identity of the unknown substances, or determine the presence of a compound under investigation as described above.

Figure 5:
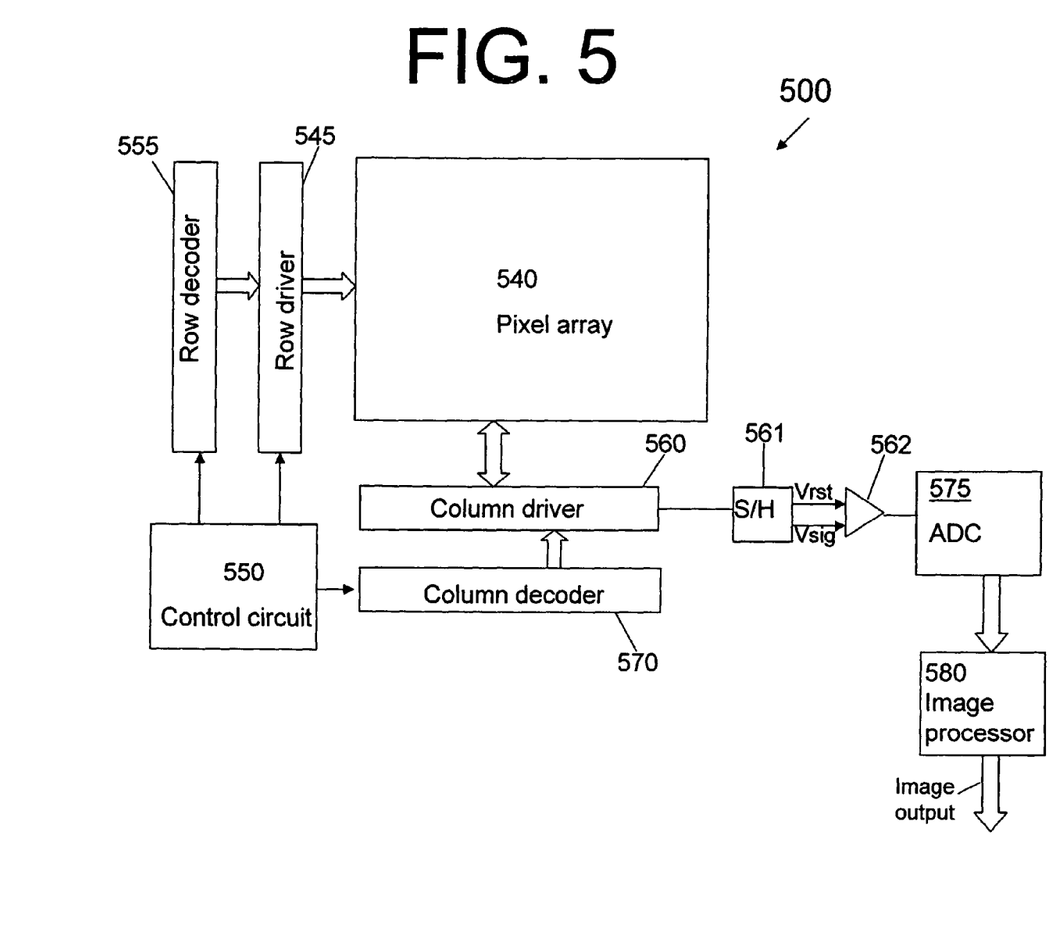
FIG. 5 shows a block diagram of an analytical imager device constructed in accordance with an exemplary embodiment of the invention.

FIG. 5 illustrates an exemplary analytical imaging device 500, which may be, or contain portions of, the analytical imaging device 134 or 134a, in accordance with one of the exemplary embodiments described above. The device 500 has a pixel array 540 comprising pixels 130 (FIG. 1.) In a preferred embodiment, at least a portion of the pixel array 540 is covered by the material layer 150. Row lines of the array 540 are selectively activated by a row driver 545 in response to row address decoder 555. A column driver 560 and column address decoder 570 are also included in the imaging device 500. The imaging device 500 is operated by the timing and control circuit 550, which controls the address decoders 555, 570. The control circuit 550 also controls the row and column driver circuitry 545, 560.

A sample and hold circuit 561 associated with the column driver 560 reads a pixel reset signal Vrst and a pixel image signal Vsig for selected pixels of the array 540. A differential signal (Vrst−Vsig) is produced by differential amplifier 562 for each pixel and is digitized by analog-to-digital converter 575 (ADC). The analog-to-digital converter 575 supplies the digitized pixel signals to an image processor 580 which forms and may output a digital image. As mentioned above, the component parts shown in FIG. 5, including the image processor 580, can be built on a single semiconductor chip for the analytical imaging device 500. A light source may also be on the single chip or external thereto. Circuitry for wireless transmission/receipt of information can also be on a chip with the analytical imaging device 500. This circuitry can be used for wirelessly transmitting data, including representations of output pixel signals, from pixels in the imaging device 500 to external processing systems or related circuitry.

Figure 6:
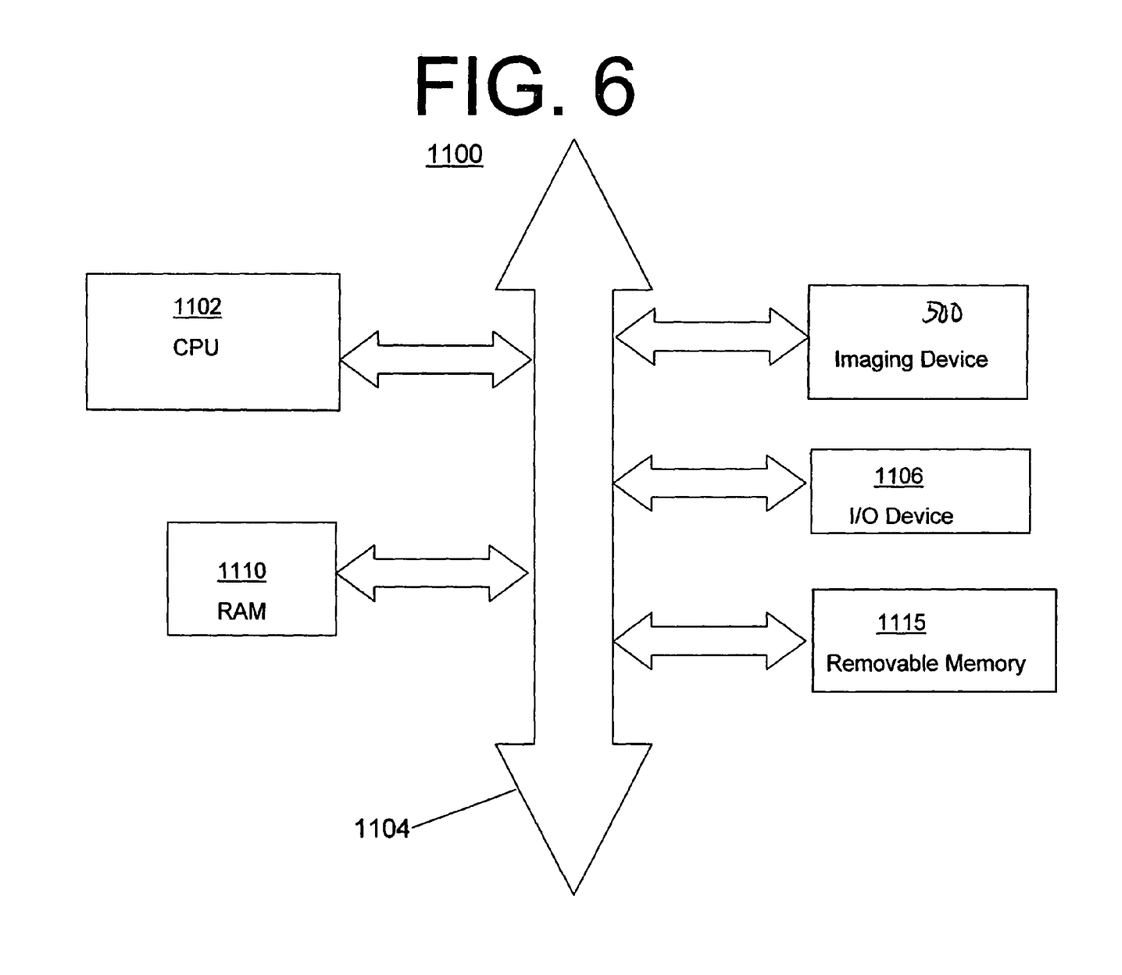
FIG. 6 shows a processor system incorporating at least one analytical imaging device constructed in accordance with an embodiment of the invention.

FIG. 6 shows system 1100, a typical processor system modified to include the imaging device 500 (FIG. 5) of the invention. The system 1100 is exemplary of a system having digital circuits that could include image sensor devices. Without being limiting, such a system could be a computer system that is used in the analytical methods described above.

System 1100 generally comprises a central processing unit (CPU) 1102, such as a microprocessor, that communicates with an input/output (I/O) device 1106 over a bus 1104. Imaging device 500 also communicates with the CPU 1102 over the bus 1104. The processor-based system 1100 also includes random access memory (RAM) 1110, and can include removable memory 1115, such as flash memory, which also communicate with the CPU 1102 over the bus 1104. The imaging device 500 may be combined with a processor, such as a CPU, digital signal processor, or microprocessor, with or without memory storage on a single integrated circuit or on a different chip than the processor.

The processes and devices described above illustrate preferred methods and typical devices of many that could be used and produced. The above description and drawings illustrate embodiments, which achieve the objects, features, and advantages of the present invention. However, it is not intended that the present invention be strictly limited to the above-described and illustrated embodiments. For example, although the embodiments are described with reference to a CMOS imager, the invention is not limited to a particular type of imager, but rather, could be used with any solid state image sensors. In addition, any modification, though presently unforeseeable, of the present invention that comes within the spirit and scope of the following claims should be considered part of the present invention.

What is claimed as new and desired to be protected by Letters Patent of the United States is:

1. An analytical system comprising:
   an imager comprising:
      a pixel array having a plurality of pixels including at least one white reference pixel and at least one black reference pixel, said white and black reference pixels being used to calibrate said analytical system; and
      at least one material layer formed over a portion of the, pixel array that does not include said white reference pixel, said material layer having optical properties which change when in the presence of one or more reactants;
   a light source for applying light to said imager through said material layer; and
   a sensing circuit for sensing a response from said imager to said applied light to detect a change in the optical properties of said material layer.

2. The system of claim 1, wherein said material layer is a plurality of different material layers.

3. The system of claim 2, wherein the identity of each of said plurality of different material layers is pre-determined, and said analytical system is designed to determine the identity of each of said one or more reactants.

4. The system of claim 2, wherein the identity of each of said one or more reactants is pre-determined.

5. The system of claim 2, wherein said plurality of different material layers are each different polymers and each of said one or more reactants is an unknown solvent.

6. The system of claim 1, wherein said imager comprises a CMOS imager and said pixel array comprises a plurality of CMOS pixel cells.

7. The system of claim 1, wherein a plurality of white reference pixels are left uncovered by said material layer.

8. The system of claim 1, wherein said black reference pixel is covered so that it is not exposed to light from said light source.

9. The system of claim 8, wherein a plurality of black reference pixels are covered.

10. The system of claim 1, wherein a plurality of light sources are applied to said imager through said material layer.

11. The system of claim 1, wherein said sensing circuit and said imager are a part of a common integrated circuit chip.

12. The system of claim 11, wherein said sensing circuit is constructed to detect a pixel output signal from each pixel in said pixel array at said first and second times.

13. An imager for detecting the presence of a chemical compound, comprising:
   an analytical imaging device, comprising:
      an imaging sensor package comprising a plurality of pixel sensors; and
      a plurality of material layers formed over a portion of said imaging sensor package, said plurality of material layers having optical properties which change when in the presence of one or more reactants and said plurality of material layers is removable from said imaging sensor package such that said imaging sensor package is reusable with a different plurality of material layers.

14. The system of claim 13, wherein said plurality of material layers is formed in one substantially planar level over said portion of said imaging sensor package.

15. The system of claim 13, wherein said plurality of material layers is formed in a plurality of stacked levels over said portion of said imaging sensor package.

16. The system of claim 13, wherein said plurality of material layers comprises an adhesive substance enabling said plurality of material layers to be attached to and removed from said imaging sensor package.

17. The system of claim 13, wherein said imaging sensor package is removable from said analytical imaging device such that said analytical imaging device is reusable with a different imaging sensor package.

18. The system of claim 8, wherein said black reference pixel is covered by underlying circuitry that prevents said black reference pixel from receiving light from said light source.

19. The system of claim 8, wherein said black reference pixel is covered by a non-transparent light shielding layer that prevents said black reference pixel from receiving light from said light source.

20. The system of claim 10, wherein said sensing circuit is constructed to sense a response of said imager to a first light source applied at a first time and to a second light source applied at a second time, wherein the first time is before exposure to said one or more reactants and the second time is after said exposure.

* * * * *